United States Patent [19]

Coffen et al.

[11] Patent Number: 4,495,354

[45] Date of Patent: Jan. 22, 1985

[54] PROCESS FOR BICYCLIC DIKETONES

[75] Inventors: David L. Coffen, Glen Ridge, N.J.; Urs O. Hengartner, Basel, Switzerland

[73] Assignee: Hoffmann-La Roche Inc., Nutley, N.J.

[21] Appl. No.: 363,332

[22] Filed: Mar. 29, 1982

[51] Int. Cl.³ .................................... C07D 217/04
[52] U.S. Cl. ...................... 546/146; 546/84; 546/149; 546/150; 546/283; 546/315
[58] Field of Search ............... 546/149, 150, 146

[56] References Cited

U.S. PATENT DOCUMENTS 4,260,762  4/1981  Berger et al. ............... 546/84
4,334,070  6/1982  Berger et al. ............... 546/70

Primary Examiner—Glennon H. Hollrah
Assistant Examiner—James H. Turnipseed
Attorney, Agent, or Firm—Jon S. Saxe; Bernard S. Leon; William G. Isgro

[57] ABSTRACT

The preparation of bicyclic diketones of the formula

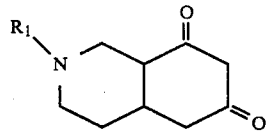

wherein $R_1$ is lower alkyl or ar-lower alkyl from a compound of the formula

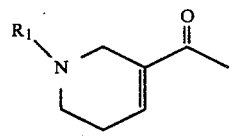

wherein $R_1$ is as previously described or a salt thereof, and a di-lower alkyl malonate is described. The reactants are combined in a reaction sequence consisting of Michael addition, cyclization, hydrolysis, and decarboxylation. The preparation of the compounds of formula II is also described.

3 Claims, No Drawings

PROCESS FOR BICYCLIC DIKETONES

BRIEF SUMMARY OF THE INVENTION

The invention relates to a process for the preparation of bicyclic diketones of the formula

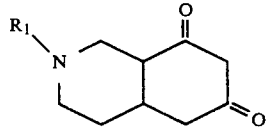

wherein $R_1$ is lower alkyl or ar-lower alkyl, which comprises reacting a compound of the formula

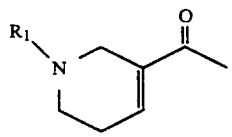

wherein $R_1$ is as previously described with a di-lower alkyl malonate in a reaction sequence that consists of Michael addition, cyclization, hydrolysis, and decarboxylation.

In another aspect, the invention relates to the preparation of a compound of the formula

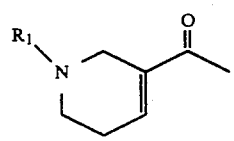

wherein $R_1$ is as previously described which comprises the N-alkylation and reduction of a compound of the formula

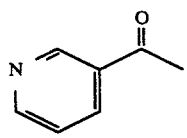

DETAILED DESCRIPTION OF THE INVENTION

The invention relates to a facile process for the preparation of bicyclic diketones. More specifically, the process comprises the reaction of a compound of the formula

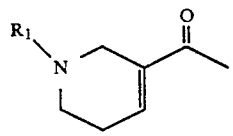

wherein $R_1$ is lower alkyl or ar-lower alkyl, with a di-lower alkyl malonate to yield a compound of the formula

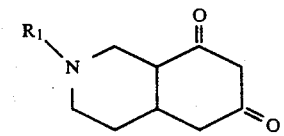

The invention also relates to the preparation of a compound of the formula

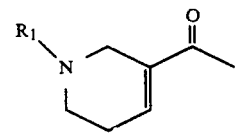

wherein $R_1$ is as previously described. The compounds of formula II are useful as intermediates in the process of the invention.

As used herein, the term "lower alkyl" denotes an alkyl group of 1 to 7 carbon atoms, for example, methyl, ethyl, propyl, isopropyl, butyl, pentyl, heptyl and the like. The term "ar-lower alkyl" denotes an aromatic hydrocarbon such as an aryl lower alkyl wherein aryl is phenyl or substituted phenyl and lower alkyl is as described herein. The substituents on the phenyl moiety may comprise one or more halogen, lower alkyl and the like. Exemplary of ar-lower alkyl are benzyl, methylbenzyl and the like.

In accordance with the invention, the process for the preparation of the compounds of formula I is carried out as set forth in Reaction Scheme I which follows:

Reaction Scheme I

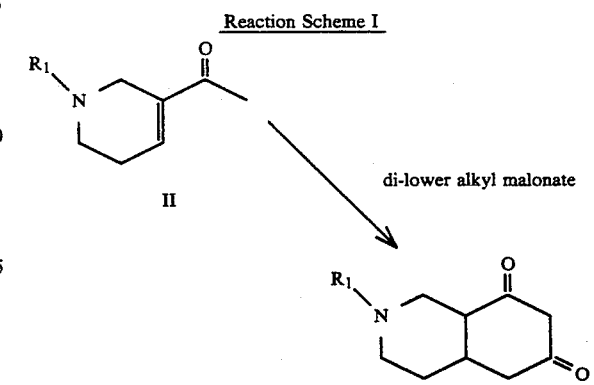

wherein $R_1$ is lower alkyl or ar-lower alkyl.

In accordance with Reaction Scheme I, a compound of formula II is reacted with a di-lower alkyl malonate, for example, dimethyl malonate, diethyl malonate and the like, in a suitable solvent, for example, a lower alkanol, such as, methanol, ethanol, propanol, butanol, t-butanol and the like, and in the presence of an alkali metal alkoxide, such as, sodium ethoxide, potassium methoxide and the like. The compounds of formula II and the di-lower alkyl malonates are known compounds or can be prepared in accordance with known procedures. Exemplary of the compounds of formula II are 1-(1,2,5,6-tetrahydro-1-methyl-3-pyridyl)ethanone, 1-(1,2,5,6-tetrahydro-1-ethyl-3-pyridinyl)ethanone, 1-(1,2,5,6-tetrahydro-1-benzyl-3-pyridinyl)ethanone and the like. At this stage of the process, a carbanion derived from the di-lower alkyl malonate undergoes Michael addition to the α,β-unsaturated ketone function of a compound of formula II. The adduct thus formed undergoes cyclization under the reaction conditions employed.

Thereafter, the reaction mixture is treated sequentially with a base, for example, an alkali metal hydroxide, such as, sodium hydroxide, potassium hydroxide and the like, and an acid, for example, an inorganic acid, such as, hydrochloric acid, hydrobromic acid and the like. This treatment effects hydrolysis and decarboxylation, respectively, of the redundant ester function introduced with the malonate to yield a hexahydro-6,8(1H,7H)-isoquinolinedione of formula I.

The process of Reaction Scheme I is carried out at a temperature in the range of from about room temperature to about the reflux temperature of the reaction mixture. The desired hexahydro-6,8(1H,7H)-isoquinolinedione can be used in the subsequent reaction without isolation and purification. Alternatively, the desired hexahydro-6,8(1H,7H)-isoquinolinedione can be recovered and purified utilizing conventional methods, for example, ion exchange chromatography and the like. The compounds of formula I are known compounds. Exemplary of the compounds of formula I are hexahydro-2-methyl-6,8(1H,7H)-isoquinolinedione, hexahydro-2-benzyl-6,8(1H,7H)-isoquinolinedione, hexahydro-2-ethyl-6,8(1H,7H)-isoquinolinedione and the like.

4-one of formula IV is recovered utilizing a conventional method, for example, by crystallization and the like. The conversion of the compound of formula I to 4,4a,5,6,7,8,8a,9-octahydro-4a,8a-trans-1H-pyrrolo[2,3-g]isoquinolin-4-one is further described in U.S. Pat. No. 4,260,762, issued Apr. 7, 1981. The 4,4a,5,6,7,8,8a,9-octahydro-4a,8a-trans-1H-pyrrolo[2,3-g]isoquinolin-4-ones are useful as antipsychotic agents, for instance, in the treatment of schizophrenia.

The process hereinafter described in Reaction Scheme III, in accordance with the invention, also forms part of the invention.

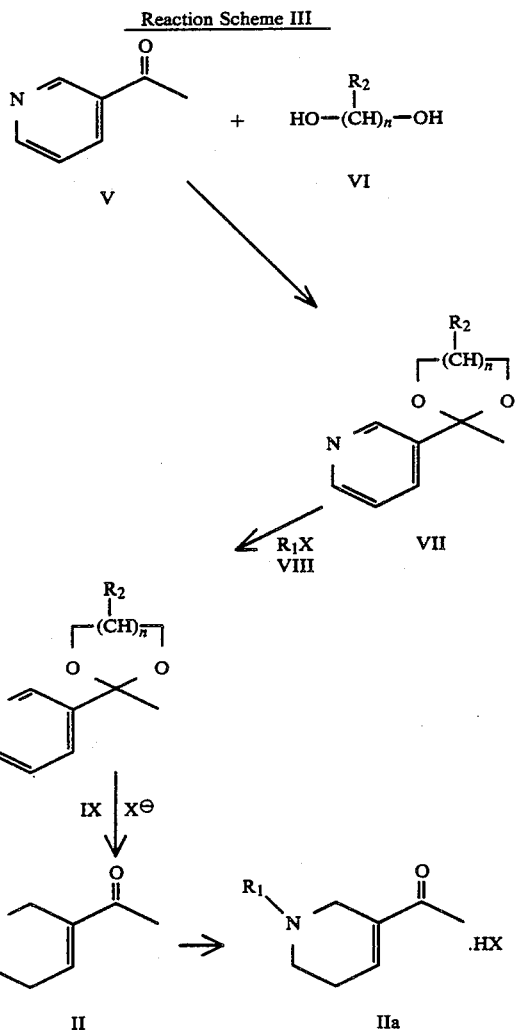

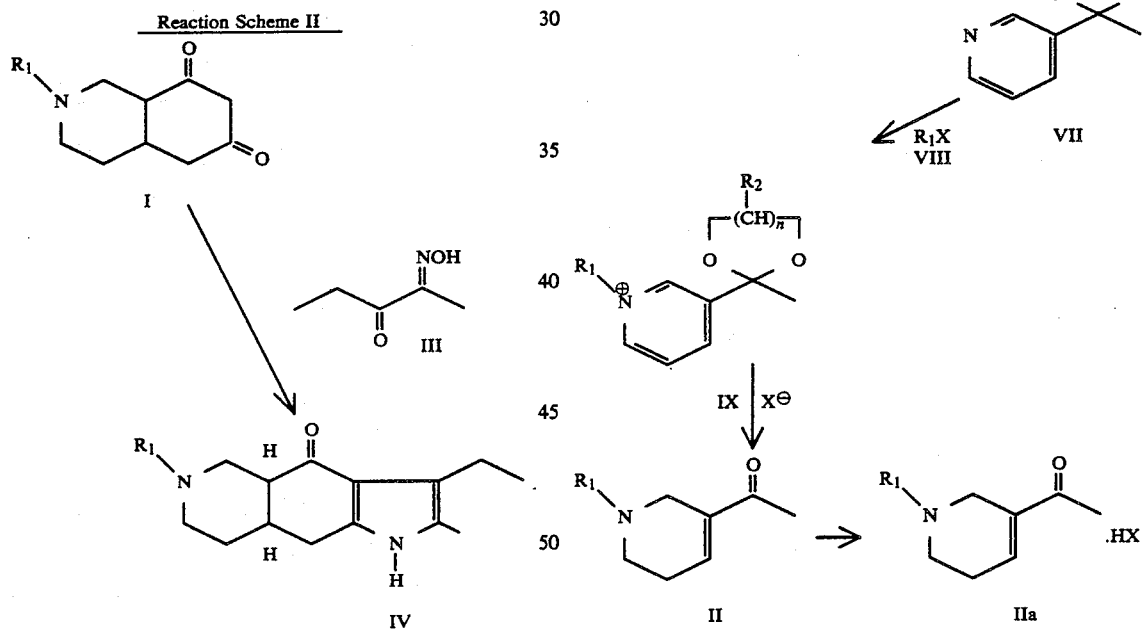

wherein $R_1$ is as previously described.

In accordance with Reaction Scheme II, a hexahydro-6,8(1H,7H)-isoquinolinedione of formula I is reacted with the 2-oximino-3-pentanone of formula III, utilizing the conditions of a Knorr pyrrole synthesis, to yield the correspondingly substituted 4,4a,5,6,7,8,8a,9-octahydro-4a,8a-trans-1H-pyrrolo[2,3-g]isoquinolin-4-one.

The reactiion is carried out in the presence of zinc dust and an acid, generally a carboxylic acid for example, acetic acid, and at a temperature in the range of from about room temperature to the reflux temperature of the reaction mixture. The desired 4,4a,5,6,7,8,8a,9-octahydro-4a,8a-trans-1H-pyrrolo[2,3-g]isoquinolinwherein $R_1$ is as previously described, $R_2$ is hydrogen and methyl, X is halogen and n is 2 to 4.

In accordance with Reaction Scheme III, 3-acetyl pyridine is treated with a glycol of formula VI in the presence of boron trifluoride etherate and the like, and an aromatic hydrocarbon solvent, for example, xylene, benzene and the like, to yield a compound of formula VII, for example, 3-(2-methyl-1,3-dioxolan-2-yl)pyridine. If desired, an obtained compound of formula VII can be used in the subsequent reaction without isolation and purification. Alternatively, a compound of formula VII can be recovered by distillation and the like.

Thereafter, a compound of formula VII is reacted with an alkyl or aralkyl halide of formula VIII to yield a pyridinium compound of formula IX. Exemplary of the halides of formula VIII are benzyl chloride, methyl iodide, ethyl bromide and the like. The reaction is carried out in an aromatic hydrocarbon solvent, for example, xylene, benzene and the like, at a temperature in the range of room temperature to the reflux temperature. The compound of formula IX usually precipitates from the reaction mixture and can be recovered by filtration.

A compound of formula IX is then, in a first step, treated with a reducing agent, for example, sodium borohydride, and an alkali metal alkoxide such as sodium methoxide and the like. The reduction is carried out in an alkanol, for example, methanol, ethanol and the like, at the reflux temperature of the reaction mixture. In a second step, the reaction mixture is treated with an acid, for example, a hydrohalic acid such as hydrochloric acid and the like, and finally made alkaline with a base such as potassium carbonate and the like, to yield a compound of formula II. If desired, a compound of formula II is converted to a salt of formula IIa for convenience of storage and handling The conversion is carried out utilizing a hydrohalic acid such as hydrobromic acid, hydrochloric acid and the like. The compounds of formula II can be recovered by extractive isolation, distillation and the like. The salts of formula IIa are generally solids and can be recovered by filtration.

The examples which follow further illustrate the invention. All temperatures are in degrees centigrade unless otherwise stated.

EXAMPLE 1

Preparation of
1-(1,2,5,6-tetrahydro-1-methyl-3-pyridinyl)ethanone

A 1-l. beaker was charged with a solution of 144.1 g of 1-(1,2,5,6-tetrahydro-1-methyl-3-pyridinyl)ethanone hydrobromide, in 400 ml of water. Then, 220 g of anhydrous potassium carbonate was added portionwise with stirring; the free base separated as a mobile oil. The mixture was extracted with 500 ml and 2×250 ml portions of chloroform.

The combined extracts were dried over anhydrous carbonate and concentrated on a rotavap (20 mm, 35°). To remove some remaining chloroform, the residual oil was taken up in 250 ml of ethylacetate and concentrated again on a rotavap leaving 101 g of 1-(1,2,5,6-tetrahydro-1-methyl-3-pyridinyl)ethanone as a yellow oil.

EXAMPLE 2

Preparation of
3-ethyl-2,6-dimethyl-4,4a,5,6,7,8,8a,9-octahydro-4a,8a-trans-1H-pyrrolo[2,3-g]isoquinolin-4-one A 3-l. three-necked flask, equipped with a mechanical stirrer, thermometer and reflux condenser was charged under nitrogen with 750 ml of absolute ethanol. 21.2 g of freshly cut sodium metal was added and the stirred mixture was slowly brought to reflux. After all the sodium had reacted, the solution was cooled to 20°. 119.5 g of diethyl malonate and 0.655 mol of the above prepared 1-(1,2,5,6-tetrahydro-1-methyl-3-pyridinyl)ethanone (101 g containing approx. 10 g solvent), were added. The solution was stirred at reflux for 5 hours.

The following day 95 g of 85% potassium hydroxide pellets were added and the mixture stirred at reflux for 4 hours. The reflux condenser was replaced by a Claisen distilling head connected to a condenser with a cooled (dry ice-acetone bath) receiver. 1.2 l of solvent was distilled at vacuo (200 mm) while 1.2 l of water was gradually added from a dropping funnel, keeping the volume of the reaction mixture constant. The solution was cooled below 60° and 400 ml of concentrated hydrochloric acid (12N) was slowly added from a dropping funnel. The resulting clear yellow solution was stirred at reflux for 1 hour. The reactor was again set for distillation (as described above) and the solution was concentrated in vacuo, first at 10 mm (aspirator vacuum), then at 4 mm (pump) leaving a very viscous semisolid paste which contains the hydrochloride salt of hexahydro-2-methyl-6,8(1H,7H)-isoquinolinedione.

This material was taken up in 1.4 l of glacial acetic acid at 50° and then cooled to 15°. 69.0 g of 2-oximino-3-pentanone, and 98.1 g of zinc dust were added. The mixture was stirred for 3 minutes at room temperature and then the moderately exothermic Knorr reaction was initiated by heating the flask content to about 45°. Without external heating, the internal temperature rose slowly over 5 minutes to 95°. The mixture was then heated at reflux for 20 minutes. The flask contents were quickly cooled to 20° in an ice bath and 57.5 g of 2-oximino-3-pentanone and 65.5 g of zinc dust were added. The resulting exothermic reaction heated the mixture to 65° (5 minutes), which was then stirred again at reflux for 20 minutes. It was quickly cooled to 20° and a third portion of 57.5 g of 2-oximino-3-pentanone and 65.5 g of zinc dust were added. After the internal temperature leveled at 65°, the reaction mixture was stirred at reflux for 1 hour. Then the reactor was set for distillation (as described above) and the brown solution concentrated at aspirator vacuum to a brown viscous oil (650 ml acetic acid was collected). 1.2 l of water was added, some residual zinc was removed by filtration and the filtrate was placed in an ice cooled 4-l. beaker. 1.5 l of concentrated ammonia (29%) was slowly added with stirring. The precipitate was collected on a coarse, sintered glass funnel and washed with 2×500 ml portions of water. The wet cake was dissolved in 1.4 l of 1.7N aqueous hydrochloric acid at 70° and the free base was again precipitated by adding 300 ml of concentrated ammonia (29%) to the warm (70°) solution. The cooled reaction mixture was filtered and the filter cake was washed with 3×1 l portions of water.

The wet cake (308 g; mp 246°-250°) was transferred into a 2-l. beaker, 1.2 l of acetone was added and the white suspension was stirred at room temperature for 30 minutes. The product was collected by filtration, washed with 500 ml of ether and dried [50°, 2 mm, 4 hr. then r.t., 0.1 mm, const. weight] to yield 73.0 g (45%) of crude 3-ethyl-2,6-dimethyl-4,4a,5,6,7,8,8a,9-octahydro-4a,8a-trans-1H-pyrrolo[2,3-g]isoquinolin-4-one as an off white powder, mp 256°-259°. This material was dissolved in 1.0 l of ethanol and 400 ml of methylene chloride at reflux. The slightly turbid brown solution was filtered through a bed of Celite which was washed with 150 ml of methylene chloride. The clear filtrate was placed in a 3-l. three-necked flask (fitted with mechanical stirrer, thermometer and Claisen distilling head connected to a condenser and a cooled receiver). 700 ml of solvent, mostly methylene chloride, was removed by distillation; toward the end of the distillation the product began to crystallize.

The mixture was allowed to cool to room temperature and was then stirred in an icebath for 2 hours. The precipitate was collected by filtration, washed with 150 ml of cold (−20°) ethanol and dried (r.t., 0.1 mm, const. weight) to yield 63.0 g (39% from 1-(1,2,5,6-tetrahydro- 1-methyl-3-pyridinyl)ethanone hydrobromide) of 3-ethyl-2,6-dimethyl-4,4a,5,6,7,8,8a,9-octahydro-4a,8a-trans-1H-pyrrolo[2,3-g]isoquinolin-4-one as slightly pink crystals, mp 262°-264°.

EXAMPLE 3

Preparation of 3-(2-methyl-1,3-dioxolan-2-yl)pyridine

A 3-l. three-necked flask equipped with a mechanical stirrer and a Dean Stark water separator with reflux condenser was charged with 228 g of p-toluenesulfonic acid monohydrate and 1.2 l of toluene. The mixture was stirred and heated at reflux for 30 minutes. A slightly orange solution was formed and 19 ml of water were collected in the separator. The heating mantle was removed and 88.6 g of ethylene glycol was added, followed by the addition of a solution of 121.1 g of 3-acetylpyridine in 150 ml of toluene over a period of 5 minutes. The resulting two phase mixture was vigorously stirred at reflux for 2 hours. An additional 9.2 g of ethylene glycol was added and stirring at reflux was continued for 1 hour (27 ml of water were collected in this 3 hour period). The reaction mixture was cooled quickly to 20° and then poured into a well stirred mixture of 1.0 l of 3N aqueous sodium hydroxide and 500 g of ice. The mixture was stirred for 5 minutes. The aqueous layer was separated and was extracted with 3×600 ml portions of toluene. Each portion of toluene extract was washed sequentially with the same 500 ml of brine. The combined toluene extracts were dried over anhydrous potassium carbonate and concentrated on a rotavap. The residual oil was distilled at vacuo, yielding 156.3 g of 3-(2-methyl-1,3-dioxolan-2-yl)pyridine as colorless mobile oil, b.p. 73°-75°/0.9 mm.

EXAMPLE 4

Preparation of 1-methyl-3-(2-methyl-1,3-dioxolan-2-yl)pyridinium iodide

A 3-l. three-necked flask, equipped with mechanical stirrer, reflux condenser and thermometer was charged under nitrogen with 155 g of 3-(2-methyl-1,3-dioxolan-2-yl)pyridine and 1.2 l of toluene. 272 g of methyl iodide was added. The mixture was stirred and heated at 53° (internal temp.) for 32 hours and then let stand at room temperature overnight. The precipitate was collected by filtration, washed with 500 ml of toluene, 500 ml of hexane and dried (r.t., 0.1 mm, const. weight) to yield 286.2 g (99.3%) of 1-methyl-3-(2-methyl-1,3-dioxolan-2-yl)pyridinium iodide as light yellow crystals, m.p. 185.5°-187° (sinters at 167°).

EXAMPLE 5

Preparation of 1-(1,2,5,6-tetrahydro-1-methyl-3-pyridinyl)ethanone

A 5-l. three-necked flask, equipped with mechanical stirrer, thermometer and reflux condenser with nitrogen inlet was charged under nitrogen with 285.8 g of 1-methyl-3-(2-methyl-1,3-dioxolan-2-yl)pyridinium iodide and 2.0 l of absolute ethanol. The suspension was stirred while 38.0 g of sodium borohydride was added in small portions over 30 minutes keeping the internal temperature at 25° with an ice bath. At this point all starting material had gone into solution. Then an additional 60 g of sodium borohydride was added in portions over 30 minutes while the internal temperature was kept at 35° with a cold water bath. The mixture was then stirred at reflux for 30 minutes. The heating mantle was removed. 1.0 l of 6N aqueous hydrochloric acid was slowly added from a dropping funnel and the white suspension stirred at reflux for 1 hour. The reflux condenser was replaced by a Claisen distilling head connected to a condenser and an ice-bath cooled receiver. 1.8 l of solvent was distilled at vacuo (180 mm, b.p. 54°-60°). Then the reaction mixture was cooled to 20° and stirred while 1.0 l of water was added, followed by portionwise addition of 900 g of anhydrous potassium carbonate ($CO_2$-evolution).

The product, which separated as a brown organic layer, was taken up in 1.0 l of ether and the aqueous layer, containing some crystalline inorganic salt, was extracted with 3/500 ml portions of ether. The combined ether extracts were dried over anhydrous potassium carbonate and concentrated on a rotavap. The residual red brown oil (132 g) was distilled at vacuo to give 114.5 g of 1-(1,2,5,6-tetrahydro-1-methyl-3-pyridinyl)ethanone as light yellow oil, b.p. 58°-75°/0.9 mm.

EXAMPLE 6

Preparation of 1-(1,2,5,6-tetrahydro-1-methyl-3-pyridinyl)ethanone hydrobromide 114.5 g of 1-(1,2,5,6-tetrahydro-1-methyl-3-pyridinyl)ethanone was placed into a 2-l. beaker and dissolved in 500 ml of absolute ethanol. The solution was stirred (mechanical stirrer) in an icebath, while 150.0 g of 48% aqueous hydrobromic acid was added dropwise from a dropping funnel at such a rate that the temperature did not exceed 25°. The resulting slurry was stirred in the icebath for 30 minutes. The precipitate was collected by filtration, washed with 2×175 ml portions of ice cold absolute ethanol and dried in vacuo (0.1 mm, 20°, const. weight) to yield 132.5 g of 1(1,2,5,6-tetrahydro-1-methyl-3-pyridinyl)ethanone hydrobromide as white crystals, m.p. 225°-226°. The filtrate was concentrated on a rotavap (50°, 15 mm) and the residual paste dissolved in 110 ml of absolute ethanol at reflux. The solution was stirred in an ice bath for 30 minutes. The precipitate collected by filtration, washed with 2×60 ml portions of ice cold absolute ethanol and dried (0.1 mm, 20°, const. weight) to yield a second crop of 14.5 g of 1-(1,2,5,6-tetrahydro-1-methyl-3-pyridinyl)ethanone hydrobromide as white crystals, m.p. 219°-221°.

EXAMPLE 7

Preparation of hexahydro-2-methyl-6,8(1H,7H)-isoquinolinedione

A 250 ml three necked flask, equipped with magnetic stirrer, reflux condenser and nitrogen inlet was charged with 80 ml ethanol. Thereafter, 2.28 g of sodium metal, freshly cut, was added and the mixture stirred till all the sodium had dissolved. Then, 12.33 g of diethylmalonate in 6 ml of ethanol, and 9.74 g of 1-(1,2,5,6-tetrahydro-1-methyl-3-pyridinyl)ethanone (arecolone) in 6 ml of ethanol, were added to the warm solution and the resulting solution was stirred and heated to reflux for 5 hours. Then, 10.2 g of 85% potassium hydroxide pellets were added and the mixture heated to reflux for four hours. During this period a heavy precipitate formed. With the aid of 50 ml water, the mixture was transferred into a 500 ml flask and concentrated at 30° and 20 mm of pressure. The residue was again concentrated from 50 ml water. It was then taken up in 100 ml water. 45 ml 12N hydrochloric acid were added and the solution was heated to reflux for 2 hours. It was then cooled and concentrated on a rotovap at 40° and 20 mm of pressure.

Purification was effected by:
(a) Ion exchange chromatography using 2M aqueous pyridine as eluent on a Dowex AG 50W-X8 column; and
(b) Recrystallization from water which afforded 3.87 g of hexahydro-2-methyl 6,8(1H,7H)-isoquinolinedione as colorless, hydroscopic crystals having a melting point of 141°–144°.

EXAMPLE 8

Preparation of the hydrochloride salt of hexahydro-2-methyl-6,8(1H,7H)-isoquinolinedione Three hundred (300) mg of hexahydro-2-methyl-6,8-(1H,7H)-isoquinolinedione were dissolved in 6 ml of ethanol with 0.2 ml of concentrated hydrochloric acid. The mixture was stirred at room temperature while 8 ml of anhydrous ether was added slowly. The mixture was then chilled in an ice bath for one hour. The precipitate was filtered, washed with cold ether and dried at room temperature and 0.2 mm of pressure for 3 days to yield 133.1 mg of the hydrochloride salt of hexahydro-2-methyl-6,8(1H,7H)-isoquinolinedione as white crystals having a melting point of 214°–217° d.

Analysis Calculated C, 55.17; H, 7.41; N, 6.43; Cl, 16.28; Found C, 55.10; H, 7.42; N, 6.41; Cl, 16.44.

We claim:

1. A process for the preparation of bicyclic diketones of the formula

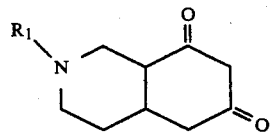

wherein $R_1$ is lower alkyl of 1 to 7 carbon atoms or phenyl-lower alkyl of 1 to 7 carbon atoms wherein phenyl can be unsubstituted or substituted by one or more groups selected from the group consisting of lower alkyl of 1 to 7 carbon atoms and halogen which comprises the steps of (a) reacting a compound of the formula

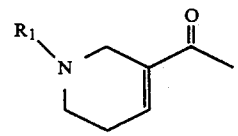

wherein $R_1$ is as previously described, or a salt thereof with a di-lower alkyl malonate, wherein lower alkyl is of 1 to 7 carbon atoms, in the presence of a lower alkanol and an alkali metal alkoxide; and (b) treating the resulting reaction mixture sequentially with a base and then with an acid.

2. A process in accordance with claim 1, wherein the compound of formula II is 1-(1,2,5,6-tetrahydro-1-methyl-3-pyridinyl)ethanone.

3. A process in accordance with claim 2, wherein the di-lower alkyl malonate is diethyl malonate.

* * * * *